United States Patent [19]

Neuman

[11] Patent Number: 5,394,883
[45] Date of Patent: * Mar. 7, 1995

[54] MULTIPLE THIN FILM SENSOR SYSTEM

[75] Inventor: Michael Neuman, Chesterland, Ohio

[73] Assignee: Case Western Reserve University, Cleveland, Ohio

[ * ] Notice: The portion of the term of this patent subsequent to Oct. 12, 2010 has been disclaimed.

[21] Appl. No.: 118,006

[22] Filed: Sep. 8, 1993

Related U.S. Application Data

[63] Continuation of Ser. No. 665,596, Mar. 5, 1991, Pat. No. 5,251,636.

[51] Int. Cl.$^6$ ............................................. A61B 5/08
[52] U.S. Cl. ................................. 128/724; 128/716
[58] Field of Search ....................... 128/716, 724–725, 128/736, 671, 639–640; 338/22 R; 29/620

[56] References Cited

U.S. PATENT DOCUMENTS

| | | | |
|---|---|---|---|
| 2,831,181 | 4/1958 | Warner | 340/213 |
| 3,232,288 | 2/1966 | Krobath | 128/724 |
| 3,241,549 | 3/1966 | Tyler | 128/724 |
| 3,452,314 | 6/1969 | Sapoff et al. | 338/22 |
| 3,884,219 | 5/1975 | Richardson et al. | |
| 3,903,876 | 9/1975 | Harris | |
| 3,906,936 | 9/1975 | Habal | |
| 3,999,537 | 12/1976 | Noiles | 128/724 |
| 4,289,142 | 9/1981 | Kearnes | 128/716 |
| 4,306,567 | 12/1981 | Krasner | 128/671 |
| 4,326,404 | 4/1982 | Mehta | 73/29 |
| 4,350,166 | 9/1982 | Mobarry | 128/664 |
| 4,366,821 | 1/1983 | Wittmaier et al. | 128/719 |
| 4,567,888 | 2/1986 | Robert et al. | |
| 4,595,016 | 6/1986 | Fertig et al. | 128/719 |
| 4,602,644 | 7/1986 | DiBenedetto et al. | 128/725 |
| 4,745,925 | 5/1988 | Dietz | 128/725 |
| 4,777,963 | 10/1988 | McKenna | 128/724 |
| 4,878,502 | 11/1989 | Dietz | 128/725 |
| 4,971,065 | 11/1990 | Pearce | 128/721 |
| 5,053,740 | 10/1991 | Schultz et al. | 338/25 |
| 5,057,811 | 10/1991 | Strott et al. | 338/22 |
| 5,069,222 | 12/1991 | McDonald, Jr. | 128/724 |
| 5,251,636 | 10/1993 | Neuman | 128/724 |

*Primary Examiner*—Lee S. Cohen
*Assistant Examiner*—Jeffrey R. Jastrzab
*Attorney, Agent, or Firm*—Nawrocki, Rooney & Silvertson

[57] ABSTRACT

A plurality of flow sensors are fabricated using thin film deposition techniques on a single substrate. The deposition is performed to provide the proper physical relationship of the individual sensors. In the preferred embodiment, the sensors are thermoresistive elements, which change resistance in response to the flow of air across the individual elements. The change in temperature of the air flow in relation to the ambient provides an indication of the flow and may be used to determine the extent of the flow. The resulting multiple sensor structure may be effectively used as a respiration detector by positioning a different sensor element at each of the airflow orifices (i.e. two nostrils and mouth) of a patient. The individual sensor elements may be electrically coupled in series.

6 Claims, 3 Drawing Sheets

MULTIPLE THIN FILM SENSOR SYSTEM

This application is a continuation of U.S. Ser. No. 07/665,596, filed Mar. 5, 1991, entitled "Multiple Thin Film Sensor System", now U.S. Pat. No. 5,251,636, issued Oct. 12, 1993.

BACKGROUND OF THE INVENTION

1. Field of the Invention

The present invention generally relates to thin film sensor technology, and more particularly, relates to thin film sensor technology for measuring breathing air flow.

2. Description of the Prior Art

It is known in the art to employ respiration sensors to monitor patients susceptible to sleep apnea and other disorders of the respiration system. U.S. Pat. No. 4,878,502 issued to Dietz discusses a breathing sensor employing a tubular passage in which a ball is free to move to break a beam of light. The ball is moved in response to the flow of air associated with the breathing of the patient. An optoelectric inhalation sensor using thin film deposition is discussed in U.S. Pat. No. 4,745,925 issued to Dietz.

Acoustic sensors for monitoring respiration are mentioned in U.S. Pat. No. 4,602,644 issued to DeBenedetto et al., and in U.S. Pat. No. 4,595,016 issued to Fertig et al. U.S. Pat. No. 4,366,821 issued to Wittmaier. et al., shows a respiration monitoring system which preferably uses a gas sensor, and U.S. Pat. No. 4,350,166 issued to Mobarry shows a video monitor. Moisture is sensed using a sodium chloride crystal in U.S. Pat. No. 4,326,404 issued to Mehta.

U.S. Pat. No. 4,306,867 issued to Krasner shows the use of a pressure sensor. An impedance plethysmograph is employed in U.S. Pat. No. 4,289,142 issued to Kearns. The use of thermoresistive sensors is suggested in U.S. Pat. No. 3,903,876 issued to Harris, U.S. Pat. No. 3,884,219 issued to Richardson et al., and U.S. Pat. No. 3,999,537 issued to Noiles.

SUMMARY OF THE INVENTION

The present invention overcomes the disadvantages found in the prior art by providing a plurality of sensors fabricated on a single substrate. It is advantageous to employ multiple sensing elements positioned at the various orifices which vent the upper airway of a patient. In the normal case, the three orifices are the two nostrils and the mouth. During sleep, these three orifices are used in various combinations, depending upon individual habits, condition of the respiratory system (e.g. colds, etc.), and physiological differences among individuals.

Fabrication of the multiple sensors on a single substrate permits ease in fixing the physical relationship of the elements at the time of manufacture. In this way the individual sensing elements are always within proper mutual alignment.

Using thin film deposition techniques, the multiple sensor system is easily and reliably fabricated. In the preferred mode, a single conductive layer of metalization having a high temperature coefficient of resistance is deposited on a nonconducting substrate. Each of the individual sensor elements consists of a large series of narrow conductive lines densely packed into a small area, which are etched in the metal film using photolithographic techniques such as .employed in the microelectronics industry. These narrow conductive lines of relatively high resistance are electrically coupled in series by very wide conductors of relatively low resistance.

Preferably all of the sensors on a substrate are electrically coupled in series fashion such that the overall resistance is changed an equivalent amount for a given airflow without regard to the orifices used for the transfer. It is also possible to measure air flow over individual sensors by using connections that measure the voltage across each of the series connected sensor elements. Air flow is measured by virtue of the difference in air temperature between ambient (inhaled) air and exhaled air. Because the substrate and the metal layer are thin and have low mass, their response to temperature changes is very rapid. This allows them to follow even the most rapid breathing rate of a small infant. The sensor can also operate in the self-heating mode whereby the current through the series connected elements is increased so that the temperature of the element is greater than the temperature of the exhaled breath. As inhaled or exhaled air moves across the sensor, it withdraws heat thereby cooling the sensor. This cooling is measured to detect breathing.

By making the active elements long and thin and the interconnecting conductive lines between active elements short and wide, a significantly greater change in resistance will occur due to temperature changes at the active sensor than at the interconnection conductors. Additionally, bending of the main substrate, which contains the wide conductors, will have little effect on resistance in comparison to the changes at the active elements due to temperature changes. Thus, the signal to noise ratio is high. Through optimized mechanical design, bending in the region of the active elements is minimized.

Preferably, fabrication of multiple sensors and conductor paths connecting the sensors from a single metalization on a single substrate allows simplicity in manufacturing. Costly soldering steps are reduced increasing reliability over discrete sensors being applied to a separate conductive circuit board.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
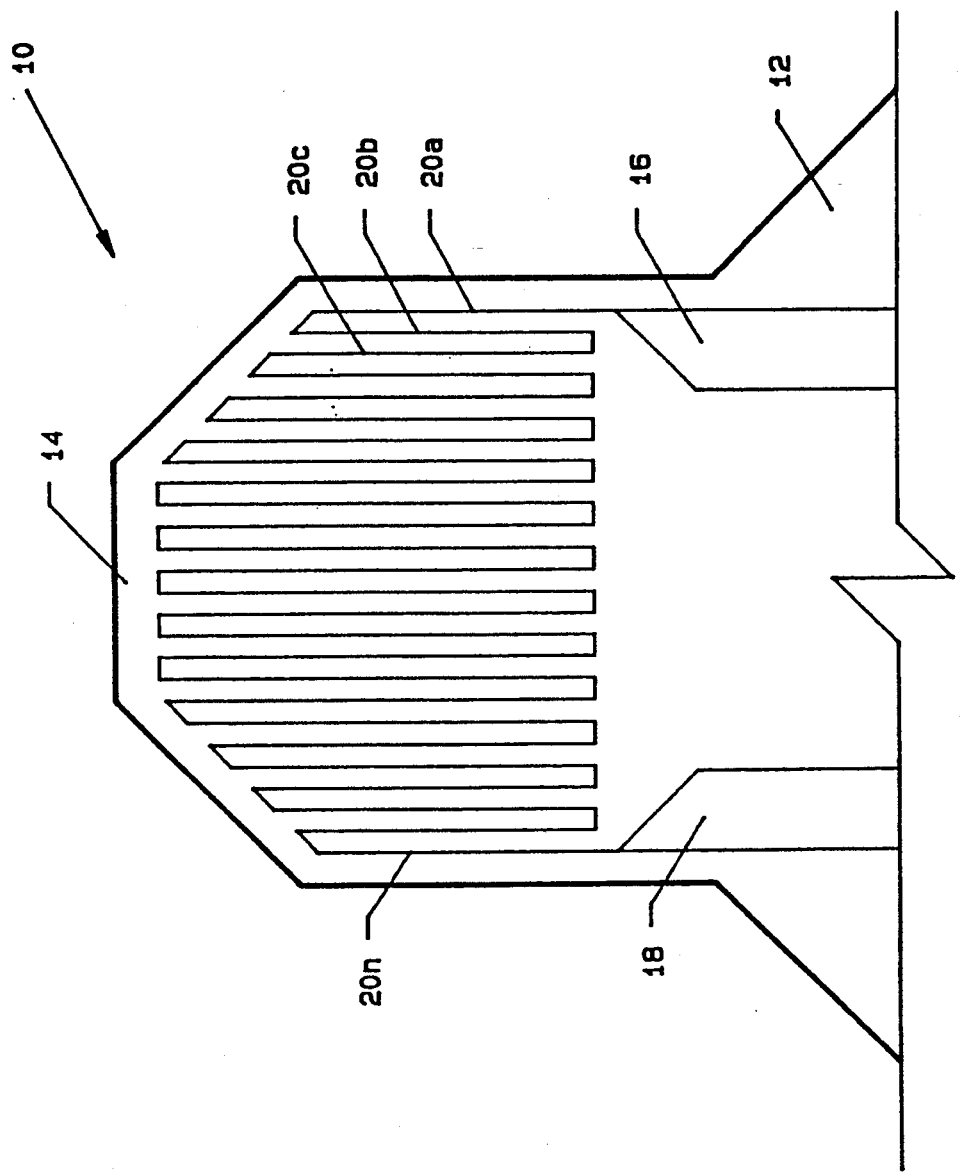
FIG. 1 is a close-up plan view of a single sensor element.

FIG. 1 is a close-up plan view of a single thermoresistive sensing element 10. Substrate 12 is an insulator such as polyimide or polyester. Upon substrate 12 is deposited a layer of conducting metalization, such as gold, having a relatively high temperature coefficient of resistance. The metalization layer provides wide conducting paths 16 and 18 to couple the sensing element into an electrical circuit as is discussed in greater detail below.

Substrate 12 has a geometrically configured portion 14 upon which is deposited the thermoresistive element. The metalization layer is configured as a series of narrow loops 20a-20n of the metalization material which are coupled in series and electrically connected to electrical conducting paths 16 and 18. The resulting structure is a thermoresistive temperature sensor. It may be used for air flow detection when a sufficient temperature difference exists between the inspired ambient air and exhaled body air. It can also detect air flow when it is heated by passing a current of higher magnitude through the element such that its temperature increases above that of the ambient inspired or expired air. Inhaled or exhaled air moving across the sensor element will cool it and change its electrical resistance.

Figure 2:
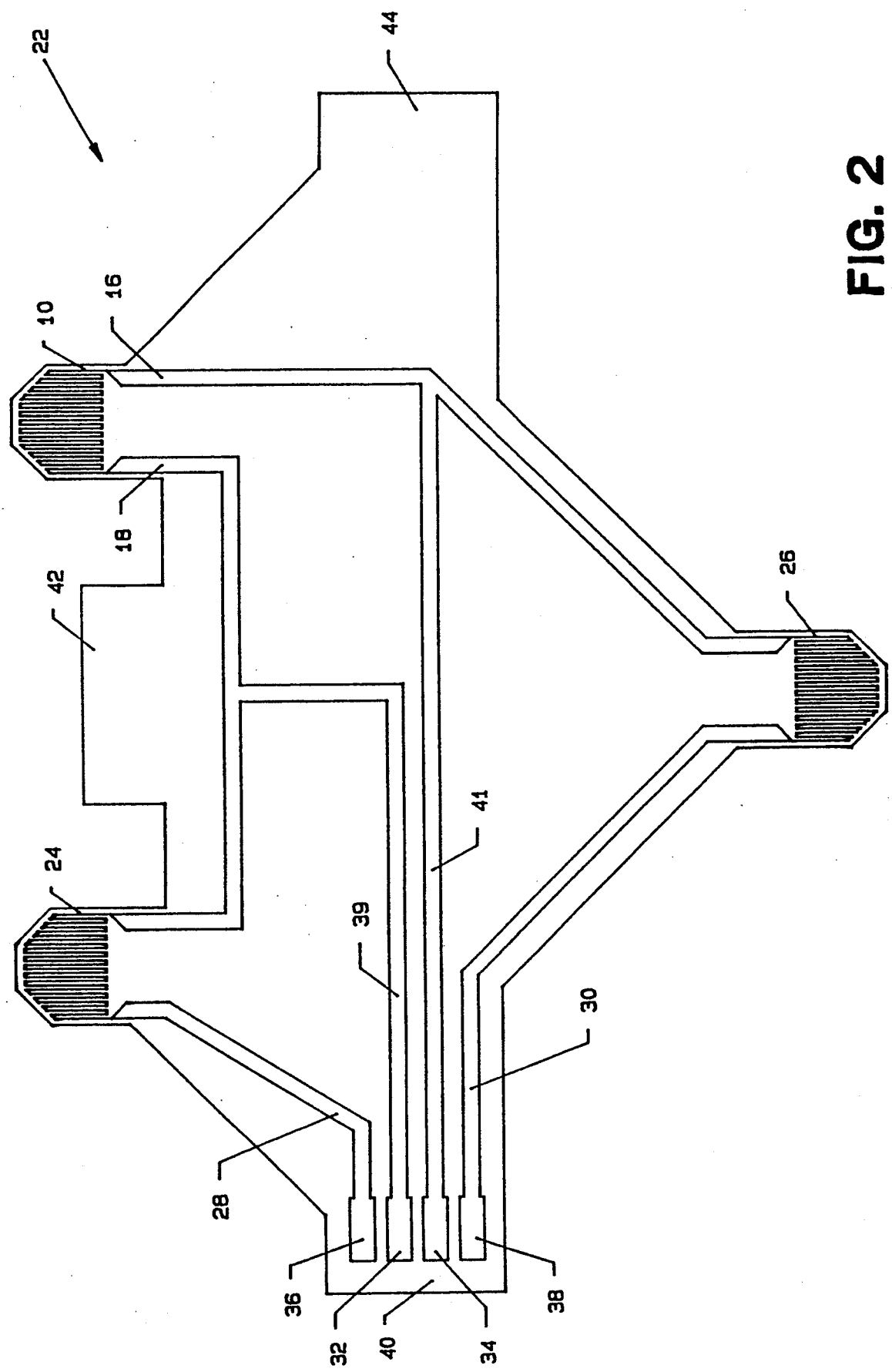
FIG. 2 is a plan view of a single substrate having multiple sensor elements; and, FIG. 3 is an electrical schematic of the multiple sensor system of FIG. 2.

FIG. 2 is a plan view of a multiple sensor system 22. In this configuration, substrate 42 contains sensing elements 10, 24, and 26. Sensing elements 24 and 26 are constructed in the same manner as sensing element 10 (see also FIG. 1).

Substrate 42 is configured to position sensing elements 10, 24, and 26 in the desired spatial relationship. Tabs 40 and 44, being configured extensions of substrate 42, provide for attachment to other structures. Sensing element 10 is electrically coupled in series with sensing element 26 by electrical conducting path 16, and in series with sensing element 24 by electrical conducting path 18.

Solder pad 36 provides for coupling of external equipment to sensing element 24 via electrical path 28. Similarly, solder pad 38 provides for coupling of external equipment to sensing element 26 via electrical path 30. Test point connector pads 32 and 34 provide for ease in individually testing each of the sensing elements. Sensing elements 10, 24, and 26; electrical paths 16, 18, 28, and 30; test point connector pads 32 and 34; and solder pads 36 and 38 are all deposited together as a single metalization layer using standard thin film photoresist/vacuum deposition techniques.

Although it is not necessary to operate the sensor with a protective layer over its surface, such a layer can be produced. This very thin layer of a polymeric insulating material, such as used for the substrate is patterned such that it does not cover the solder pads or the test point connector pads. These windows can be produced using a photo definable polymer or by other photolithographic techniques. This layer can be important as an electrical insulator to protect the sensor from conductive liquids and in providing mechanical protection to avoid scratches in the metal film that could interrupt the electrical circuit.

Figure 3:
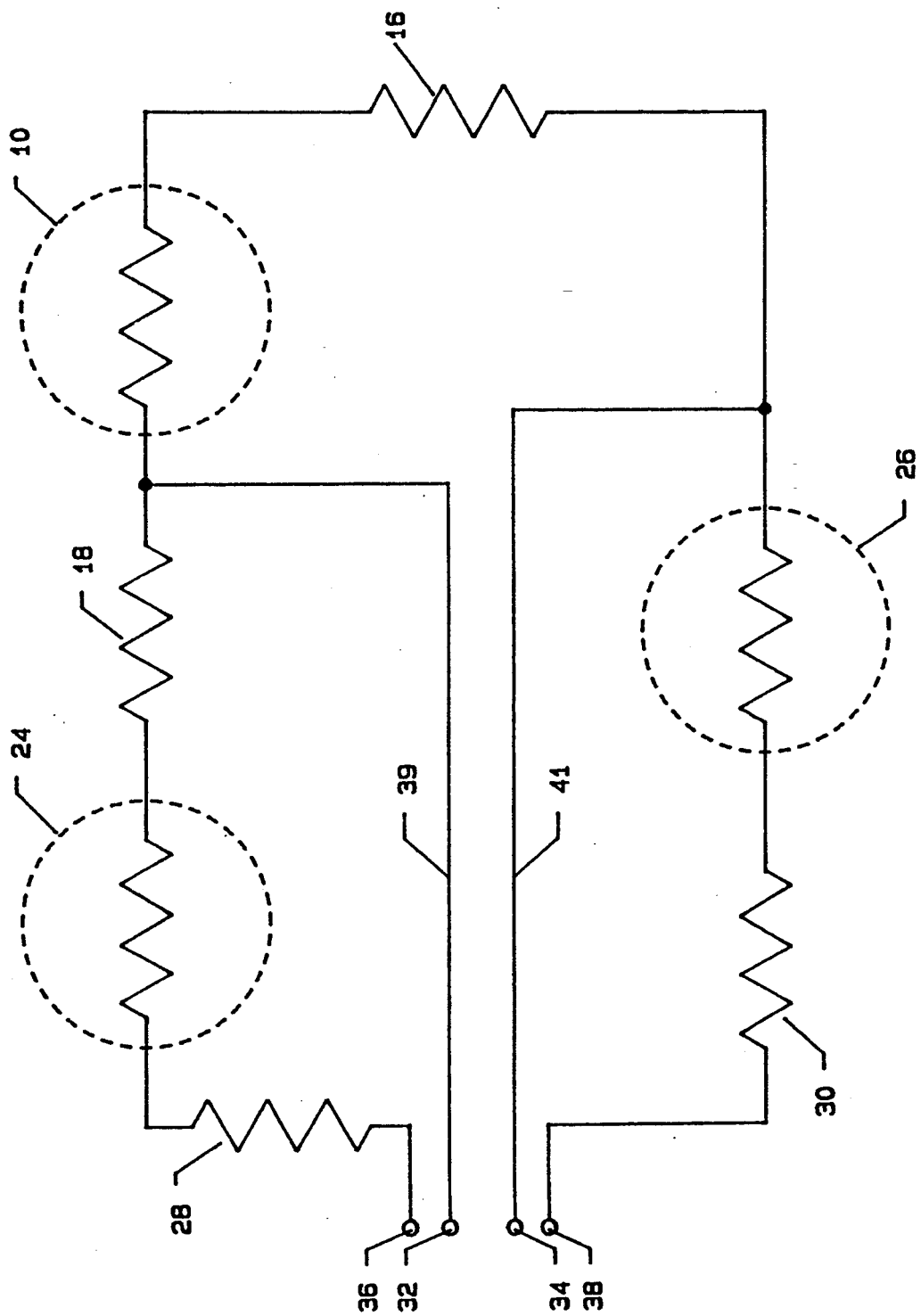

FIG. 3 is an electrical schematic diagram of multiple sensor system 22. All referenced elements are as previously described. Electrical soldering pads 36 and 38 are coupled to resistance measuring equipment to complete the circuit. Sensing elements 10, 24, and 26 function as series resistors each having a relatively large resistance which varies with temperature. As stated above, air flow can be detected if the temperature of the exhaled air is sufficiently different from ambient. Electrical conducting paths 16, 18, 28 and 30 are shown schematically to reflect the distributed resistance which is low relative to the resistance of sensing elements 10, 24 and 26.

Respiration monitoring is accomplished by applying a constant current between solder pads 36 and 38 and measuring the voltage changes. When it is desired to measure the temperature change seen at individual elements, conductor films 39 and 41 and test point pads 32 and 34 can be used. The voltage across 38 and 34 will be related to the temperature of element 26; the voltage across 34 and 32 will be related to the temperature of element 10; and the voltage across 36 and 32 will be related to the temperature of element 24. The system has a constant component associated with the fixed resistance and a component which varies with respiration. Preferably, the total current is maintained in the range of 0.1 ma to 0.5 ma to prevent excessive heat generation from the circuit. When using the self-heating mode, higher current will be necessary.

Having thus described the preferred embodiments of the present invention, those of skill in the art with be readily able to apply the teachings found herein to yet other embodiments within the scope of the claims hereto attached.

I claim:

1. A sensor apparatus comprising:
   a. a bendable substrate;
   b. a plurality of sensing elements deposited on and fixedly attached to the substrate;
   c. each of the plurality of sensing elements including a thin layer of conductive material; and
   d. another conductive material deposited on and fixedly attached to the substrate and electrically coupling the sensing elements.

2. The apparatus of claim 1 in which the substrate comprises an insulator.

3. The apparatus of claim 2 in which the plurality of sensing elements are electrically coupled in series.

4. The apparatus of claim 3 in which all of the plurality of sensing elements conductive materials comprise the same conductive material.

5. The apparatus of claim 4 in which the conductive materials have a relatively high temperature coefficient of resistance.

6. The apparatus of claim 1, 2, 3, 4 or 5 in which the plurality of sensing elements are placed in predetermined relationship to one another to permit monitoring of respiration airflow of a patient.

* * * * *